(12) United States Patent
Ikhlef

(10) Patent No.: US 11,786,195 B2
(45) Date of Patent: Oct. 17, 2023

(54) MULTI-SPHERICAL DETECTOR FOR CT SYSTEM

(71) Applicant: Minfound Medical Systems Co. Ltd., Hangzhou (CN)

(72) Inventor: Abdelaziz Ikhlef, Hudson, OH (US)

(73) Assignee: Minfound Medical Systems Co. Ltd., Hangzhou (CN)

( * ) Notice: Subject to any disclaimer, the term of this patent is extended or adjusted under 35 U.S.C. 154(b) by 219 days.

(21) Appl. No.: 17/410,446

(22) Filed: Aug. 24, 2021

(65) Prior Publication Data

US 2023/0063271 A1 Mar. 2, 2023

(51) Int. Cl.
*A61B 6/03* (2006.01)
*A61B 6/00* (2006.01)

(52) U.S. Cl.
CPC ............ *A61B 6/4233* (2013.01); *A61B 6/032* (2013.01); *A61B 6/4291* (2013.01); *A61B 6/4435* (2013.01)

(58) Field of Classification Search
CPC ..... A61B 6/032; A61B 6/4085; A61B 6/4411; A61B 6/4452; A61B 6/03; A61B 6/06; A61B 6/4233; A61B 6/4014; A61B 6/4078; A61B 6/4266; G01N 23/046
See application file for complete search history.

(56) References Cited

U.S. PATENT DOCUMENTS

2021/0052237 A1 2/2021 Yu et al.

FOREIGN PATENT DOCUMENTS

| CN | 101291627 A | 10/2008 | |
| JP | 2013192951 A | * 9/2013 | ........... G06T 11/006 |

* cited by examiner

*Primary Examiner* — Don K Wong
(74) *Attorney, Agent, or Firm* — Fishman Stewart PLLC

(57) ABSTRACT

A detector assembly for a CT system includes a first support structure having a first plurality of mini-module support surfaces, each of the first plurality of mini-module support surfaces being tangent to a hypothetical sphere that is formed having a center of the hypothetical sphere positioned at a focal spot of the CT system, the first plurality of mini-module support surfaces at a first distance from the center of the hypothetical sphere, and a second support structure positioned next to the first support structure and having a second plurality of mini-module surfaces, the second support structure being angled in an X-Y plane with respect to the first support structure such that the second plurality of mini-module surfaces are tangent to the hypothetical sphere and at the first distance from the center of the hypothetical sphere.

20 Claims, 8 Drawing Sheets

MULTI-SPHERICAL DETECTOR FOR CT SYSTEM

TECHNICAL FIELD

This disclosure relates generally to diagnostic imaging and, more particularly, to an a spherical apparatus and method for CT imaging.

BACKGROUND

Typically, in computed tomography (CT) imaging systems, a rotatable gantry includes an x-ray tube, detector, data acquisition system (DAS), and other components that rotate about a patient table that is positioned at the approximate rotational center of the gantry. X-rays emit from the x-ray tube, are attenuated by the patient, and are received at the detector. The detector typically includes a photodiode-scintillator array of pixelated elements that convert the attenuated x-rays into visible light photons within the scintillator, and then to electrical signals within the photodiode. The electrical signals are digitized and then received and processed within the DAS. The processed signals are transmitted via a slipring (from the rotational side to the stationary side) to a computer for image reconstruction, where an image is formed.

The gantry typically includes a pre-patient collimator that defines or shapes the x-ray beam emitted from the x-ray tube. X-rays passing through the patient can cause x-ray scatter to occur, which can cause image artifacts. Thus, x-ray detectors typically include an anti-scatter grid (ASG) for collimating x-rays received at the detector.

Third generation multi-slices CT scanners typically include detectors having scintillator/photodiodes arrays. These detectors are positioned in an arc where the focal spot is the center of the corresponding circle. These detectors generally have scintillation crystal/photodiode arrays, where the scintillation crystal absorbs x-rays and converts the absorbed energy into visible light. A photodiode is used to convert the light to an electric current. The reading is typically linear to the total energy absorbed in the scintillator.

Typically, CT systems obtain raw data and then reconstruct images using various known pre-processing and post-processing steps to generate a final reconstructed image. That is, CT systems may be calibrated to account for x-ray source spectral properties, detector response, and other features, to include temperature. Raw x-ray data are pre-processed using known steps that include offset correction, reference normalization, and air calibration steps, as examples.

In recent years, the development of volumetric or cone-beam CT technology has led to an increase in the number of slices used in CT detectors for computed tomography systems. The detector technology used in large coverage CT enables greater coverage in patient scanning by increasing the area exposed, by using back-illuminated photodiodes. A typical detector includes an array of 16, 32, or 64 slices. However, the need for cardiac imaging has become of greater interest to enable imaging of the heart within one rotation of the detector, substantially increasing the width of the detector in the Z-axis (e.g., along the patient length), leading to a detector having 256 or more slices. Because it is impractical to build very large modules in monolithic structure to cover this number of slices and this width in the Z-axis, due to manufacturing cost and reliability concerns, smaller modules (mini-modules) are built along the Z-axis and placed along the Z-axis to build the overall length of 256 or more slices.

That is, because it is difficult to build very large modules in monolithic structure to cover this number of slices, for reasons such as manufacturing cost and reliability, smaller modules (mini-modules) are stacked in the z-axis, and thus achieve different coverage needs. This architecture typically includes accurate processes in stacking and classification of mini-modules, with a precise mechanical packaging which enable precise alignment, removability and reparability.

Detector assemblies have been developed that include 'mini-modules', and support structures are arranged so that the mini-modules may be of the same design and placed along the Z-axis, thus allowing for a single design to be built and tested, without having to build special modules for the center vs ends of the detector (along the Z-axis, for example).

However, due to the flat nature of the mount structure on which the mini-modules are placed, placement of the modules proximate one another results in slight angular offset from the focal spot for modules that are placed off-axis (in the Z-direction). A module sub-structure used to mount several detector mini-modules along the Z-direction includes a flat surface that, for off-axis locations from the center, do not face generally perpendicular to the focal spot. Thus, for mini-modules placed away from the center yet on a flat surface, a slight but significant angular offset results, and the mini-modules are not directed toward the focal spot. This results in loss of signal efficiency, as the slight angle resulting from the angular offset casts a slight shadow from the collimator elements that are generally directed toward the focal spot.

The issue can be resolved and reduced, to a degree, by providing second or stepped surfaces for mounting the mini-modules that are angled with respect to the first. As an example, a center set of four mini-modules may be positioned along the Z-axis and on a flat first surface whose center is perpendicular to the focal spot. The mini-modules offset from the two centermost mini-modules on this first surface will thereby be slightly off-kilter or not aimed directly toward the focal spot. The offset nature in Z is exacerbated or compounded for additional modules (such as if the flat surface is arranged to include six or eight mini modules), as the mini-modules typically include collimators that are generally directed or aimed toward their center and thereby are positioned to be each centered on the focal spot when positioned centermost on the first flat surface.

Second surfaces positioned to either side of the first surface (and offset in the Z-direction) are likewise angled slightly with respect to the first surface and have their centers, as well, perpendicular to the focal spot. Being flat surfaces, mini-modules positioned on the second surfaces may, likewise, not all aim toward the focal spot. Again, a mini-module positioned in a center of the second surface may have its collimators directed toward the focal spot, but mini-modules positioned to either side may not have their collimators aimed toward the focal spot.

Another option is to fabricate individualized mini modules that are particular to each Z location on the detector assembly. However, such an arrangement would preclude swapping out mini-modules with one another, which presents logistical problems for fabricating replacement mini-modules for conducting repairs, as well as logistical challenges during detector fabrication and assembly itself. Often, mini-modules are characterized or classified after fabrication, and those meeting higher performance standards (i.e., image quality, noise, etc. . . . ) are selected for use in the center of the detector. Individual designs of mini-modules may preclude this arrangement, not to mention the overall cost increases that may be experienced having the several types of mini module designs that would be needed in this sort of arrangement.

Further, known structures include multiple modules in the Z-direction, and for curved surfaces along Z, detector modules that are positioned side-by-side (in X) include gaps that accumulate in X, due to the offset and stepped arrangement of the modules in the Y direction. That is, due to the curved arrangement in Z and for modules facing generally toward the focal spot, a gap occurs in X between module assemblies that varies along the Z direction.

Thus, there is a need to improve CT detector designs.

BRIEF DESCRIPTION

Embodiments are directed toward a multi-spherical detector for a CT system.

A detector assembly for a CT system includes a first support structure having a first plurality of mini-module support surfaces, each of the first plurality of mini-module support surfaces being tangent to a hypothetical sphere that is formed having a center of the hypothetical sphere positioned at a focal spot of the CT system, the first plurality of mini-module support surfaces at a first distance from the center of the hypothetical sphere, and a second support structure positioned next to the first support structure and having a second plurality of mini-module surfaces, the second support structure being angled in an X-Y plane with respect to the first support structure such that the second plurality of mini-module surfaces are tangent to the hypothetical sphere and at the first distance from the center of the hypothetical sphere.

A method of assembling a detector assembly for a CT system includes providing a first support structure having a first plurality of mini-module support surfaces, each of the first plurality of mini-module support surfaces being tangent to a hypothetical sphere that is formed having a center of the hypothetical sphere positioned at a focal spot of the CT system, the first plurality of mini-module support surfaces at a first distance from the center of the hypothetical sphere, providing a second support structure having a second plurality of mini-module surfaces, and positioning the second support structure to be angled in an X-Y plane with respect to the first support structure and such that the second plurality of mini-module surfaces are tangent to the hypothetical sphere and at the first distance from the center of the hypothetical sphere.

A CT system includes a rotatable gantry having an opening for receiving an object to be scanned, an x-ray tube having a focal spot from which x-rays emit, and a detector assembly comprising one or more scintillator modules for receiving x-rays from the focal spot. The detector assembly includes a first support structure having a first plurality of mini-module support surfaces, each of the first plurality of mini-module support surfaces being tangent to a hypothetical sphere that is formed having a center of the hypothetical sphere positioned at a focal spot of the CT system, the first plurality of mini-module support surfaces at a first distance from the center of the hypothetical sphere, and a second support structure positioned next to the first support structure and having a second plurality of mini-module surfaces, the second support structure being angled in an X-Y plane with respect to the first support structure such that the second plurality of mini-module surfaces are tangent to the hypothetical sphere and at the first distance from the center of the hypothetical sphere.

Various other features and advantages will be made apparent from the following detailed description and the drawings.

DETAILED DESCRIPTION

The operating environment of disclosed embodiments is described with respect to a sixteen-slice computed tomography (CT) system. Embodiments are described with respect to a "third generation" CT scanner, however it is contemplated that the disclosed embodiments are applicable to other imaging systems as well, and for CT systems having more or less than the illustrated sixteen-slice system.

Figure 1:
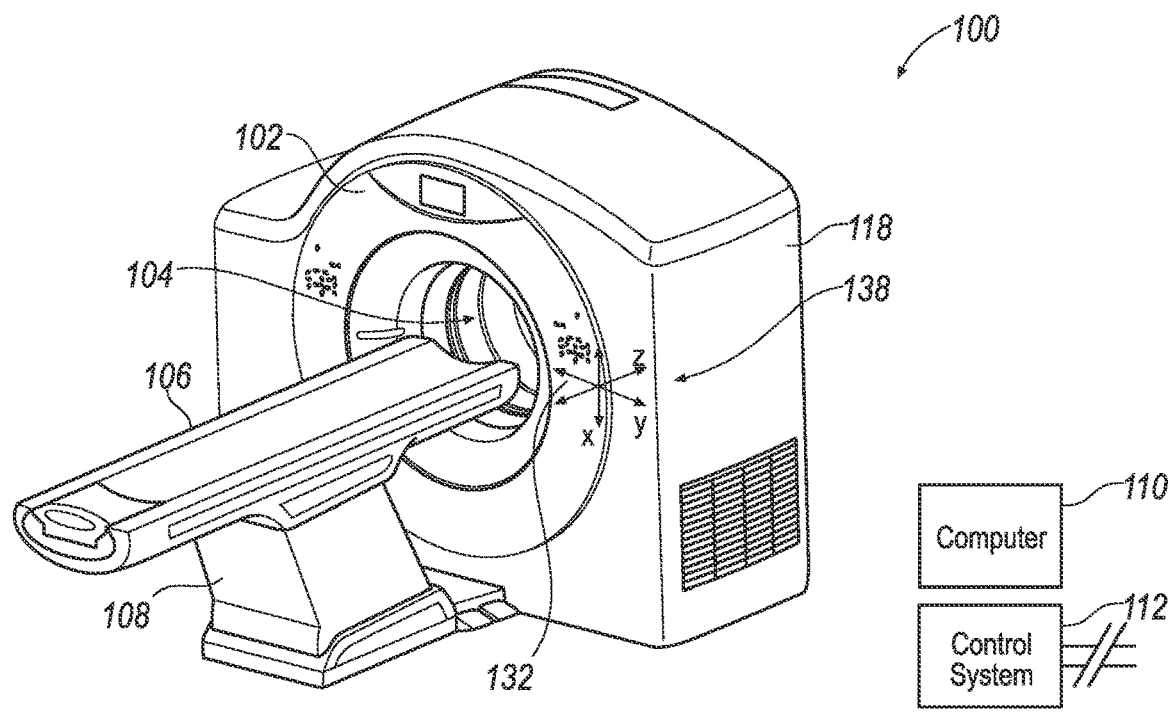
FIG. 1 is a perspective view of a CT imaging system.
Figure 2:
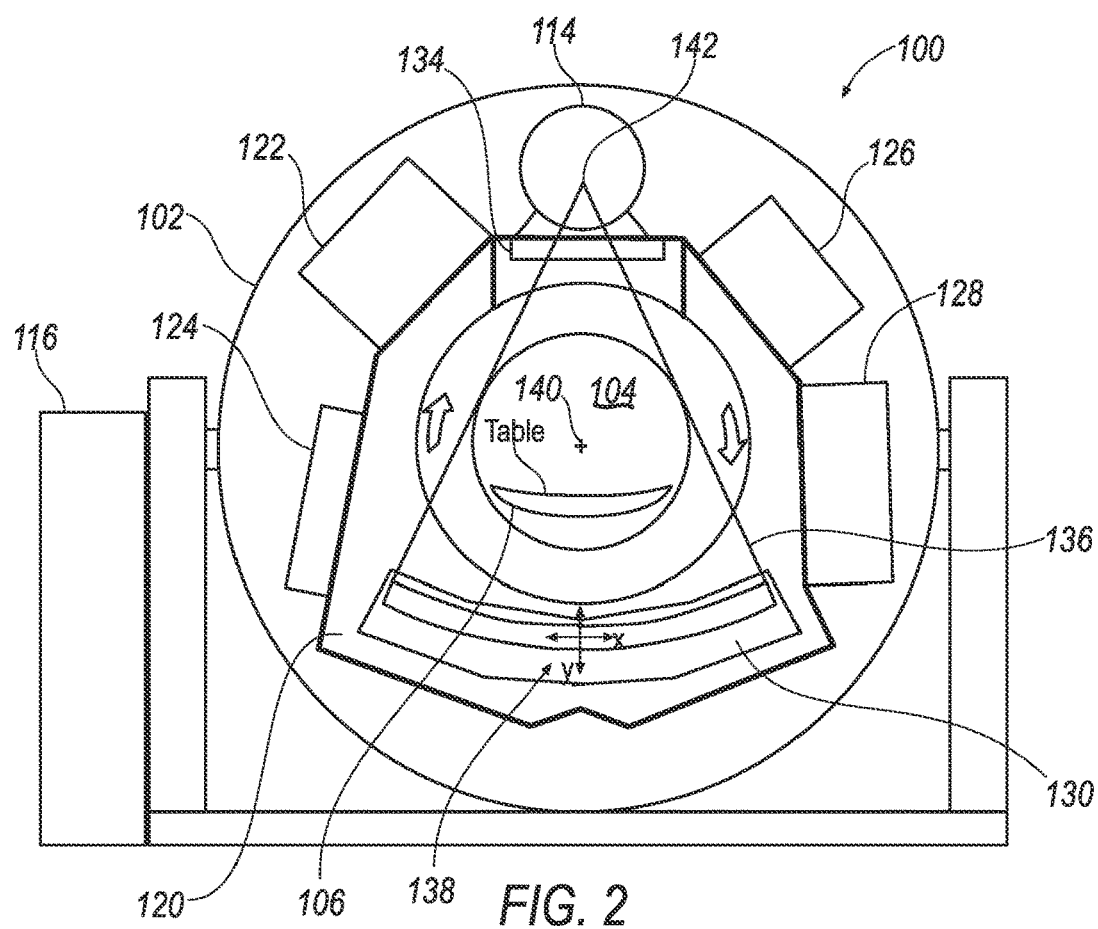
FIG. 2 is a planar cross-section of the system illustrated in FIG. 1.

Referring to FIGS. 1 and 2, a computed tomography (CT) system 100 includes a gantry 102 having an opening 104. A patient table 106 is positioned on a support structure 108, and patient table 106 is axially controllable such that a patient (not shown) positioned on table 106 may be positioned within opening 104. A computer system 110 provides operator instructions and other control instructions to a control system 112. Computer system 110 also may include image reconstruction algorithms, or an image reconstructor may be provided as a separate processing unit. Control system 112 provides control commands for operating gantry 102, an x-ray tube 114, and a gantry motor controller 116, as examples. Gantry 102 includes a cover or enclosure 118, which provides for aesthetic improvement, safety, etc.

Gantry 102 includes a rotatable base 120, on which is mounted x-ray tube 114, a heat exchanger 122, a data acquisition system (DAS) 124, an inverter 126, a generator 128, and a detector assembly 130, as examples. System 100 is operated with commands entered by a user into computer 110. Gantry 102 may include gantry controls 132 located thereon, for convenient user operation of some of the commands for system 100. Detector assembly 130 includes a plurality of detector modules (not shown), which include an anti-scatter grid (ASG), scintillators, photodiodes, and the like, which detect x-rays and convert the x-rays to electrical signals, from which imaging data is generated. Gantry 102 includes a pre-patient collimator 134 that is positioned to define or shape an x-ray beam 136 emitted from x-ray tube 114. Although not shown, a shape filter may be positioned for instance between x-ray tube 114 and pre-patient collimator 134.

In operation, rotatable base 120 is caused to rotate about the patient up to typically a few Hz in rotational speed or more, and table 106 is caused to move the patient axially within opening 104. When a desired imaging location of the patient is proximate an axial location where x-ray beam 136 will be caused to emit, x-ray tube 114 is energized and x-ray beam 136 is generated from a focal spot within x-ray tube 114. The detectors receive x-rays, some of which have passed through the patient, yielding analog electrical signals that are digitized and passed to DAS 124, and then to computer 110 where the data is further processed to generate an image. The imaging data may be stored on computer system 100 and images may be viewed. An X-Y-Z triad 138, corresponding to a local reference frame for components that rotate on rotatable base 120, defines a local directional coordinate system in a gantry circumferential direction X, a gantry radial direction Y, and a gantry axial direction Z. Accordingly, and referring to triad 138, the patient passes parallel to the Z-axis, the x-rays pass along the Y axis, and the rotational components (such as detector assembly 130) rotate in a circumferential direction and in the X direction, and about an isocenter 140 (which is a centerpoint about which rotatable base rotates, and is an approximate position of the patient for imaging purposes). A focal spot 142 is illustrated within x-ray tube 114, which corresponds to a spot from which x-ray beam 136 emits.

Figure 3:
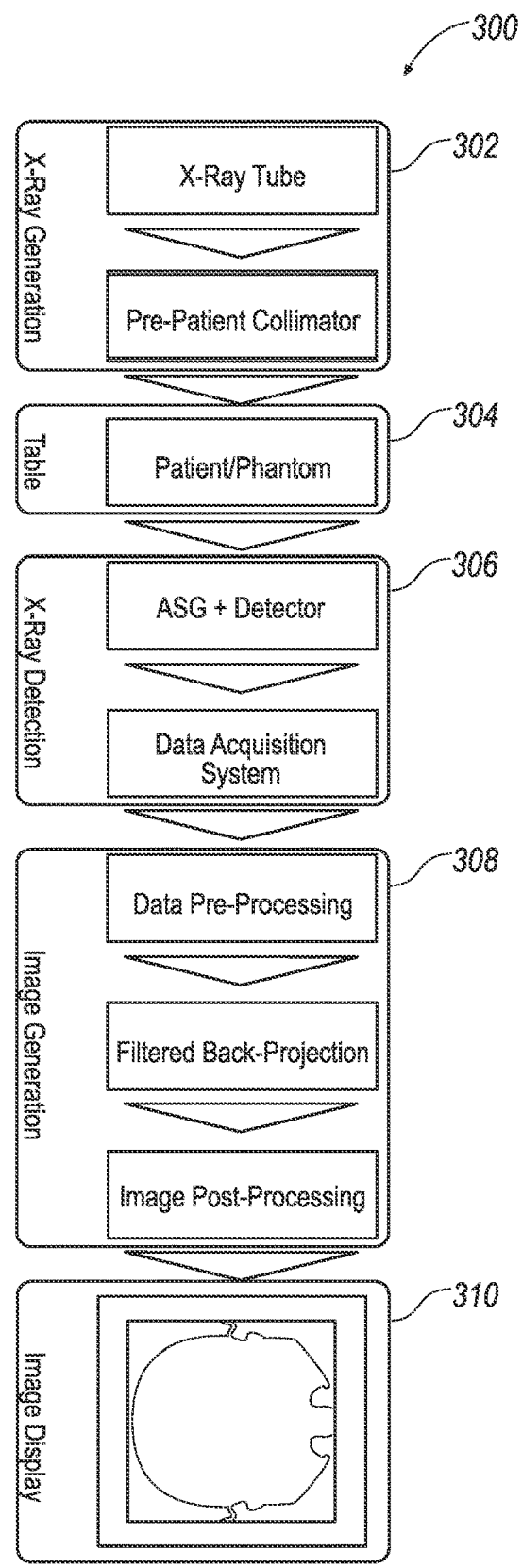
FIG. 3 is an example of an imaging chain.

FIG. 3 illustrates an exemplary image chain 300, consistent with the operation described with respect to FIGS. 1 and 2. X-ray generation 302 occurs, using x-ray tube 114 and passing x-rays through pre-patient collimator 134, during which timetable 106 passes 304 through opening 104 of gantry 102. In one example table 106 may have a patient thereon, and in another example a phantom may be used for calibration purposes.

X-ray detection 306 occurs when x-rays having emitted from x-ray tube 114 pass to detector assembly 130. An anti-scatter grid (ASG) prevents x-ray scatter (emitting for example from the patient as secondary x-rays and in a direction that is oblique to x-ray beam 136), by generally passing x-rays that emit from x-ray tube 114. DAS 124 processes signals received from detector assembly 130. Image generation 308 occurs after the digitized signals are passed from a rotating side of gantry 102 (on rotatable base 120) to a stationary side, via for instance a slipring.

Image generation 308 occurs in computer system 110, or in a separate processing module that is in communication with computer system 110. The data is pre-processed, and image views or projections are used to reconstruct images using known techniques such as a filtered backprojection (FBP). Image post-processing also occurs, after which the images may be displayed 310, or otherwise made available for display elsewhere (such as in a remote computing device).

Figure 4:
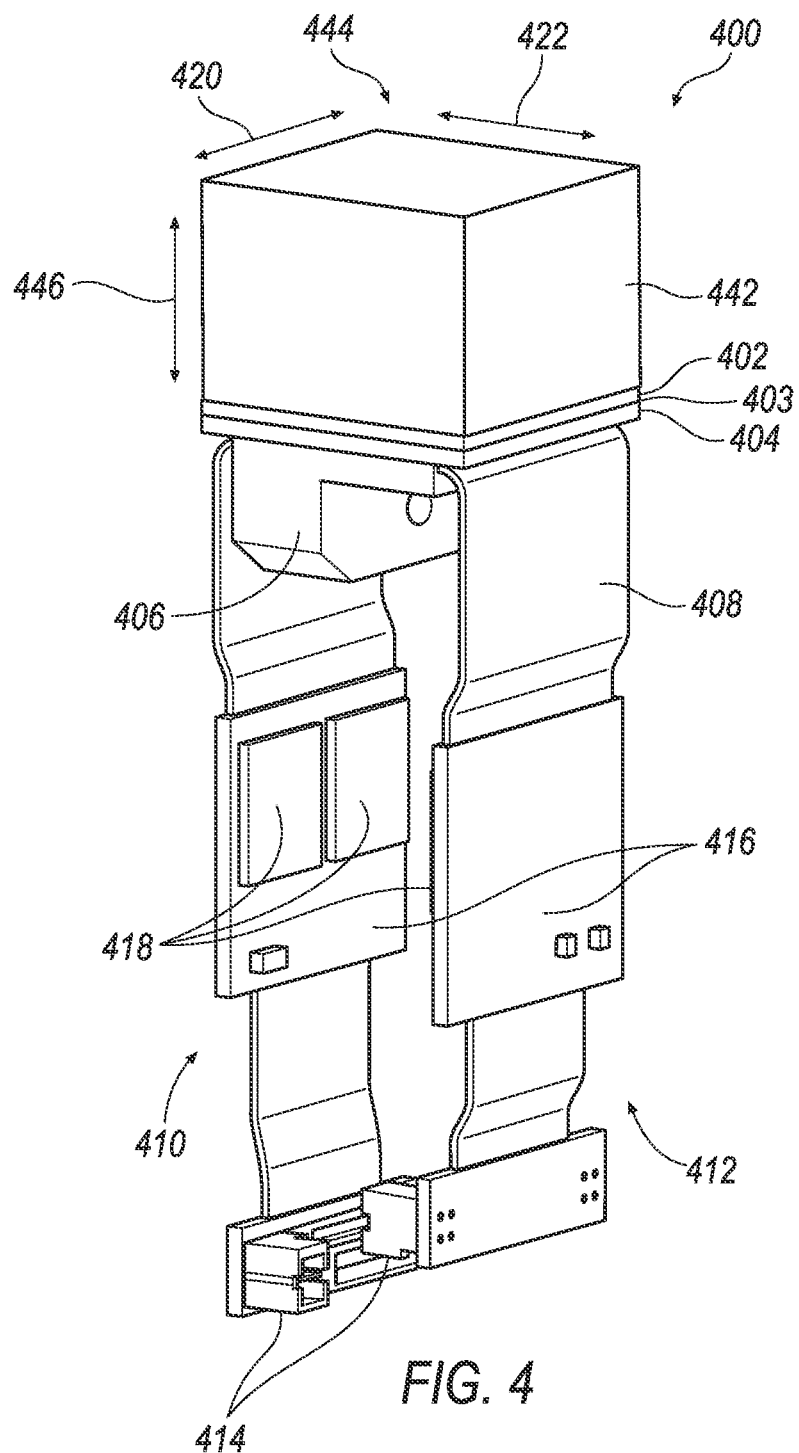
FIG. 4 illustrates a module or mini-module having a collimator attached thereto.

FIG. 4 illustrates a mini-module 400 having been assembled according to the disclosure. Mini-module 400 includes a grid of pixelated scintillators or scintillating array 402 positioned on a substrate 404, having a photodiode 403 therebetween. An alignment block or support structure 406 mechanically supports mini-module 400. Positioned between support structure 406 and substrate 404 is a flex circuit 408, which wraps within module 400 and includes a first end 410 and a second end 412. Each end 410, 412 includes electrical connectors 414, a circuit board or electronics package 416, ASIC or processors 418, and other associated electronic components (not shown). Mini-module 400, when placed on a gantry of a CT system, such as system 100 above, in one example, has an orientation of a Z or slice direction 420 and an X or channel direction 422.

An anti-scatter grid 442 having a plurality of plates 444 is positioned on an upper surface of scintillating array 402. In the example shown, anti-scatter grid 442 is a monolithic device having plates that extend in X or channel direction 422, or may have plates that extend in both X or channel direction 422, as well as a Z or slice direction 420. Anti-scatter grid 442 in the illustrated example may be fabricated using a plurality of tungsten plates, or as another example may be fabricated using 3D printing technology and having high density materials such as tungsten or other x-ray absorbing materials therein. Accordingly, in one example, anti-scatter grid 442 is a two-dimensional (2D) collimator with plates 444 spaced from one another having a spacing that corresponds with a spacing of pixels.

Plates 444 may thereby be fabricated in anti-scatter grid 442 to be slightly non-parallel to one another so that each may be directed and approximately aimed toward a focal spot of a CT system. For instance, referring to FIG. 2, mini-modules 400 may be positioned accordingly within CT detector assembly 130 and on gantry 102, having each plate 444 extending along a length and in a direction 446 such that, when CT detector 130 is positioned in CT system 100, the length of plates 444 extend 446 approximately toward focal spot 142 of CT system 100.

Figure 5:
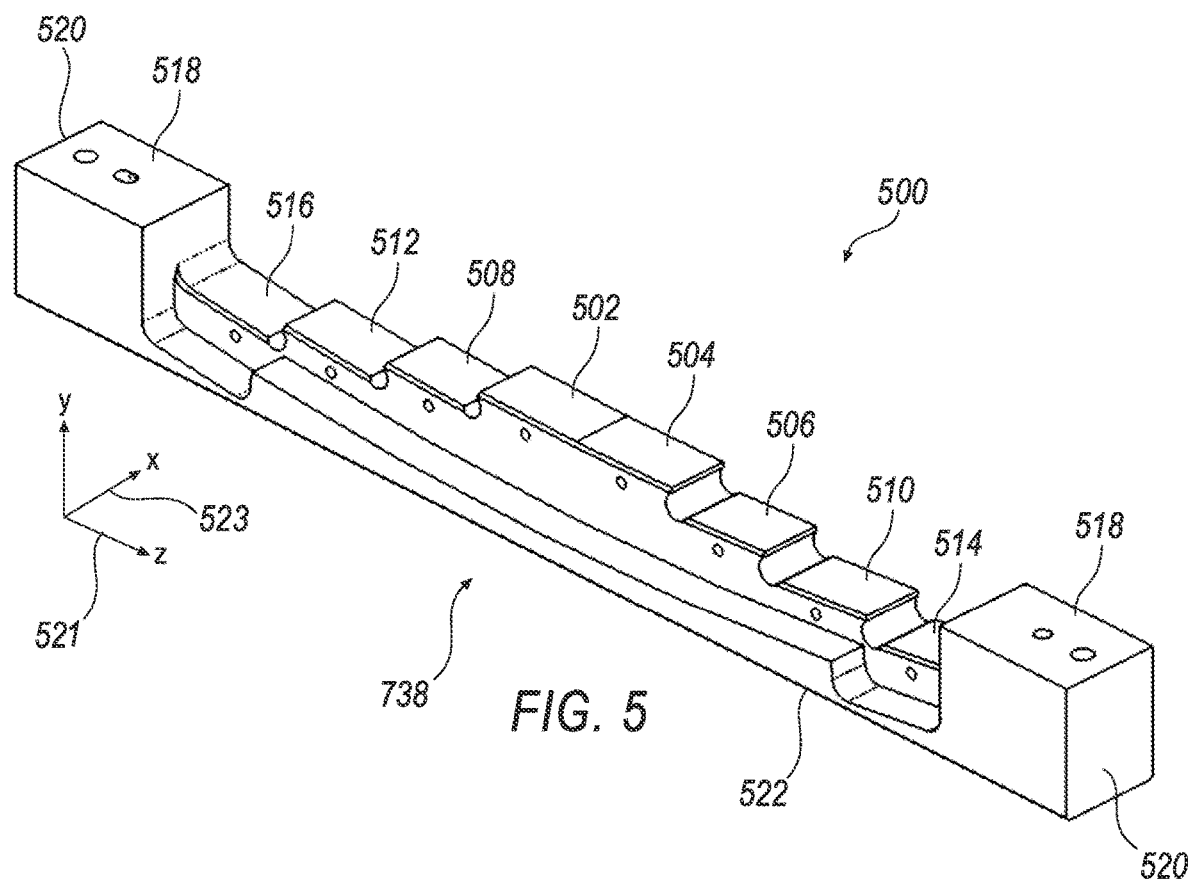
FIG. 5 illustrates a detector support structure.

FIG. 5 illustrates an alignment block or support structure 500 for a detector assembly for a CT system. Support structure 500 includes mini-module support surfaces 502, 504, that are positioned at a first distance from focal spot 142, mini-module support surfaces 506, 508 that are positioned at a second distance from focal spot 142, mini-module support surfaces 510, 512 that are positioned at a third distance from focal spot 142, and mini-module support surfaces 514, 516 that are positioned at a fourth distance from focal spot 142. Support structure includes detector mount surfaces 518 for mounting support structure 500 in the larger detector assembly, as will be further discussed.

Figure 6:
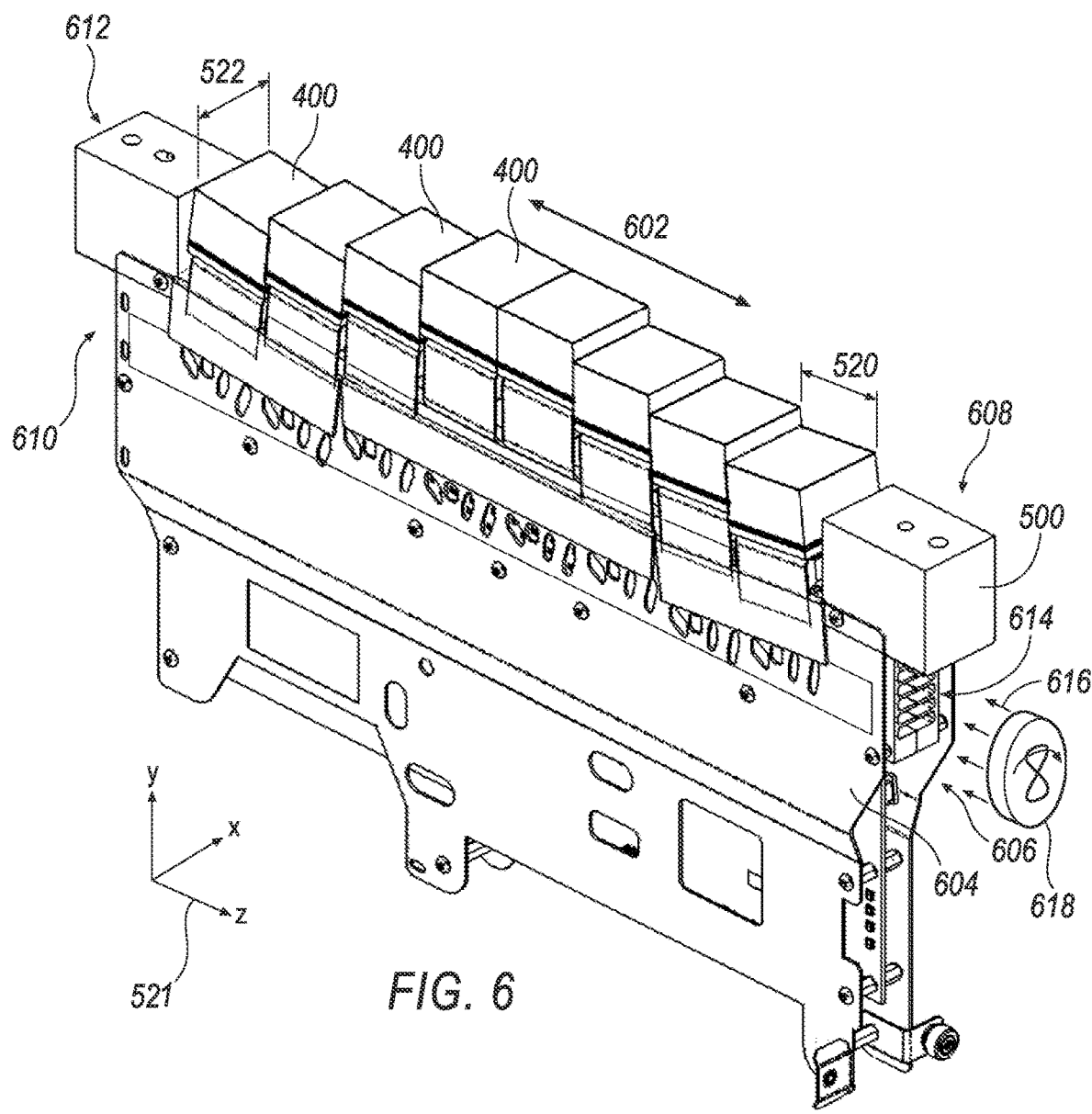
FIG. 6 illustrates a detector sub-assembly having a plurality of modules on the detector support structure of FIG. 5.

Referring now to FIG. 6, a detector sub-assembly (module) 600 shows a plurality of mini-modules 400, positioned on support structure 500. As shown, each mini-module 400 includes Z or slice direction 521, which combine to provide a composite coverage in a system Z direction 602, which corresponds with triad 138 in FIGS. 1 and 2. Correspondingly, each mini-module 400 includes X or channel direction 523, and mini-modules 400 are thereby combined or stacked side-by-side to form a plurality of detectors, corresponding with triad 138 of FIGS. 1 and 2, forming detector assembly 130. Thus, according to the disclosure, each mini-module 400 is fabricated in the fashion described herein. As such, global system tolerances do not accumulate, such as if all plates 444 were placed with respect to support structure 500, for example. In addition, each module 400 may be classified and placed within the detector according to the measured quality of the modules.

Thus, according to the disclosure, detector assembly 600 for CT system 100 includes plurality of detector mini-modules 400, each detector module including a grid of pixelated scintillators 402, a reflector (as is commonly known), a photodiode 403 having pixelations that correspond with the pixelated scintillators 402, and an electronics package 416 for processing acquired X-ray data. Support structure 500, corresponding with support structure 406 above, extends along Z-direction 602 of CT system 100 and includes a plurality of detector mini-modules 400 positioned thereon. A cover 604 extends along Z-direction 602 and includes support structure 500 mounted thereon. Cover 604 encloses a passageway 606 passing therethrough and along Z-direction 602, such that cooling air may pass into passageway 606 at a first end 608 of cover 604 and exit passageway 610 at a second end 612 of cover 604 opposite first end 608. Cover 604 encloses a plurality of fins or plates 614 positioned within passageway 606 and are thermally coupled to cover 604 and other elements, each of plurality of plates 614 extending along Z-direction 602. As such, air or another cooling medium 616 is blown into passageway 606 via a fan, as an example, represented by element 618 in FIG. 6.

Figure 7:
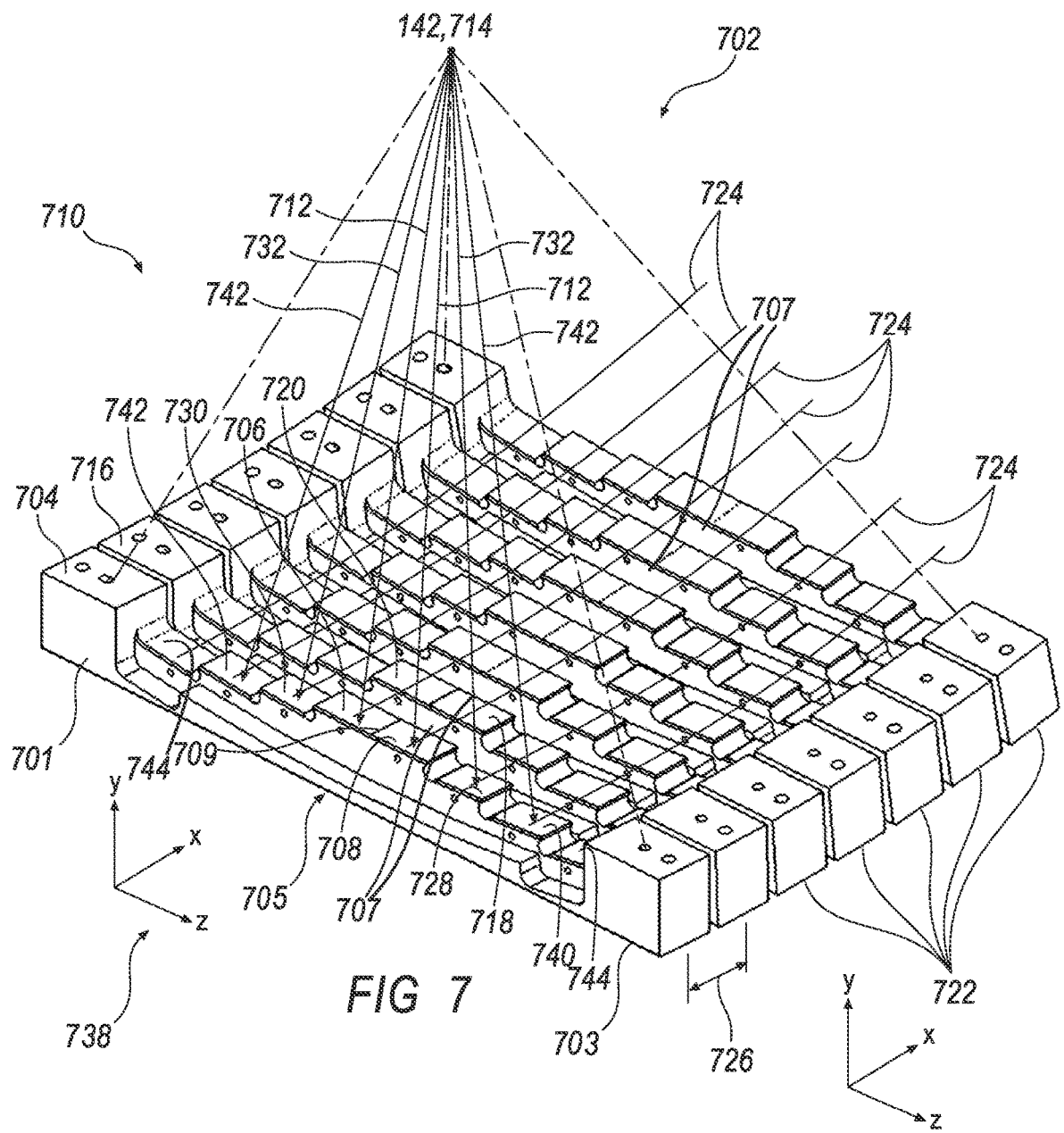
FIG. 7 illustrates a plurality of detector support structures side-by-side.
Figure 8:
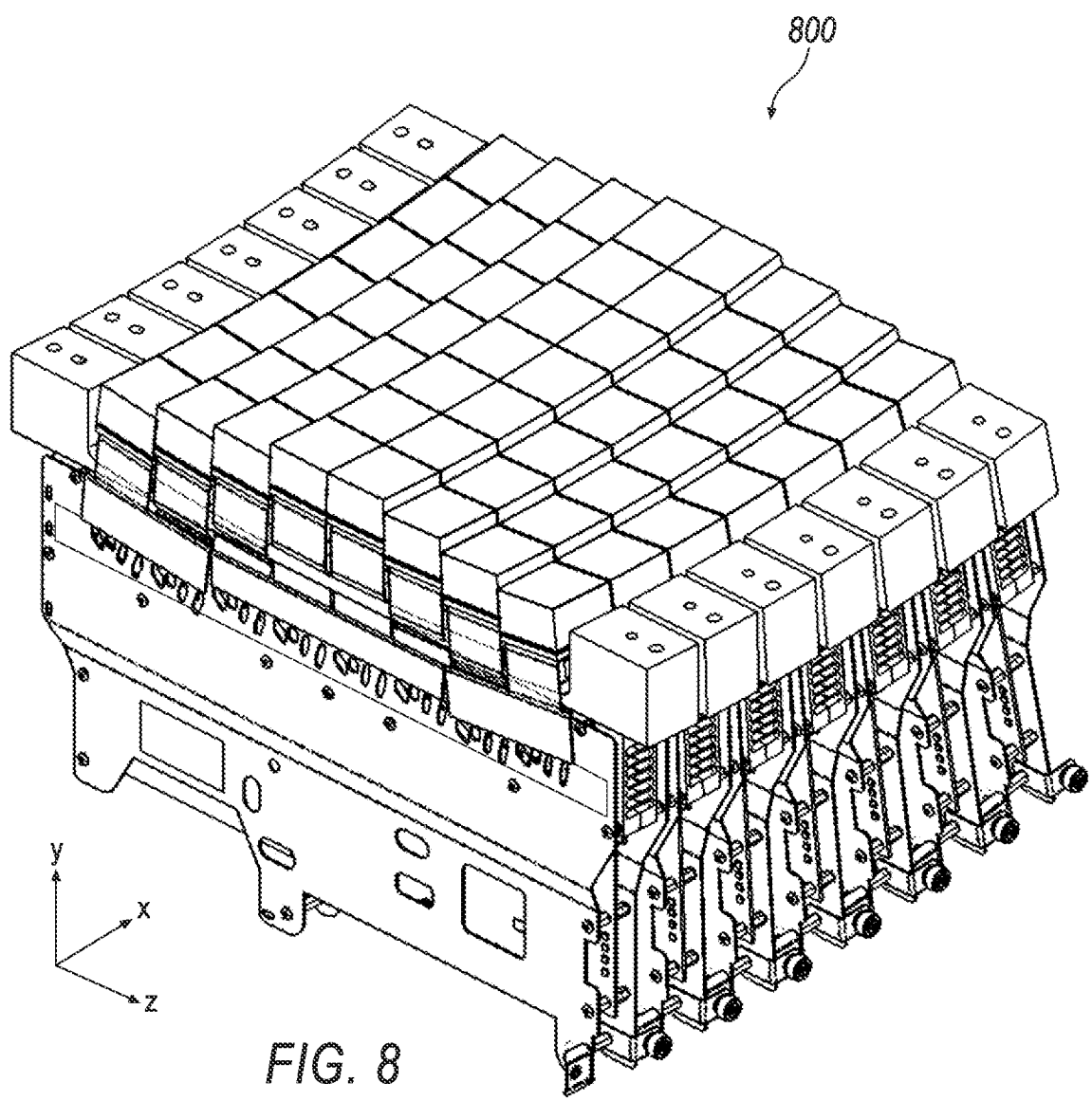
FIG. 8 illustrates a plurality of detector sub-assemblies side-by-side and each having a plurality of modules.
Figure 9:
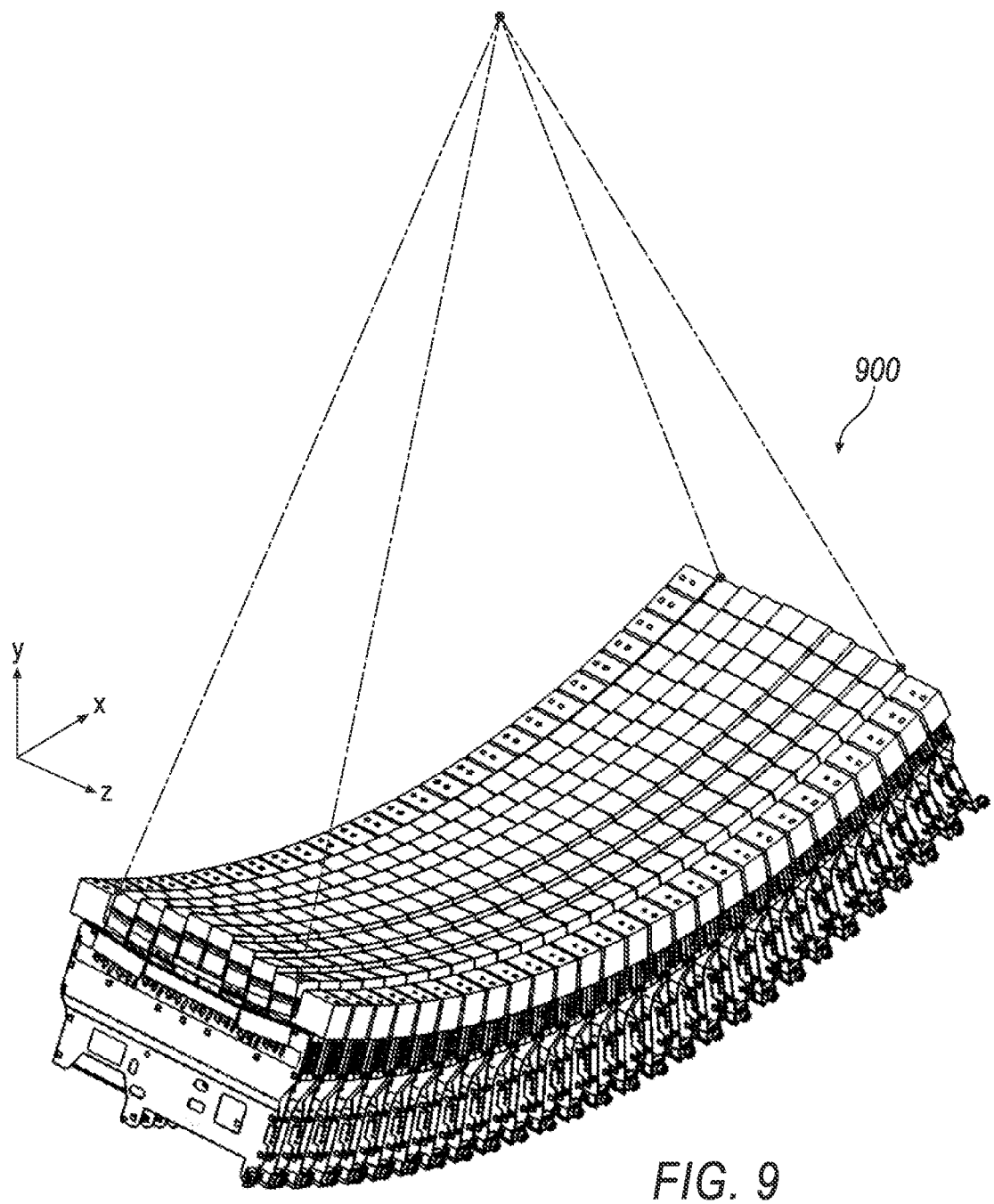
FIG. 9 illustrates a perspective view of a CT detector.

Referring to FIGS. 7, 8, and 9, a plurality of detector support structures are positioned side-by-side and illustrate a spherical detector for a CT system according to the disclosure. FIG. 7 shows a sub-set of seven (7) support structures 500 positioned side-by-side, FIG. 8 shows the sub-set of seven (7) structures having mini-modules 400 mounted thereon, and including heat sink and other structures as discussed in FIG. 6, and FIG. 9 illustrates a perspective view of a CT detector having all support structures 500, and corresponding to detector assembly 130 of FIG. 1. The detector assembly of FIG. 9 is referred to generally as detector assembly 700 and includes a plurality of support structures 702, a sub-set of which is shown in FIG. 7.

Detector assembly 700 includes a support structure 704 having a plurality of mini-module support surfaces, 706, 708, each of plurality of mini-module support surfaces 706, 708 being tangent to a hypothetical sphere 710 that is formed having a center 712 of hypothetical sphere 710 positioned and corresponding with focal spot 142 of CT system 100. Plurality of mini-module support surfaces 706, 708 is at a distance 712 from center 714 of hypothetical sphere 710 and surfaces 706, 708 are thereby tangent to hypothetical sphere 710 at the surface locations. That is, hypothetical sphere 710, having its center 714, includes hypothetical rays 712 thereby that are each orthogonal to surfaces 706, 708, and likewise pass through the center two surfaces of the neighboring support structures, as well. Thus, a second support structure 716 is positioned next to support structure 704 and having a plurality of mini-module surfaces 718, 720, second support structure 716 being angled in an X-Y plane with respect to support structure 704 such that plurality of mini-module surfaces 718, 720 are tangent to hypothetical sphere 710 and also at distance 712 from center 714 of hypothetical sphere 710. And, as evidenced by the curved or spherical nature of support structure 500, gaps in neighboring detectors form as a function of circumferential location and along the Z direction. That is, along the Z-direction, gaps form in X between neighboring support structures 722. This can be visualized by considering that if each stepped surface for neighboring support structures 722 along Z were actually at the same radius from focal spot 142/714, then placing the support structures 722 side-by-side would result in detector mini-modules being placed near each other in the extremes along Z (i.e., toward a first end 701 and a second end 703), but to avoid neighbor-to-neighbor interferences between support structure 722, then a significant gap would form at exemplary locations 707 therebetween.

Thus, according to the disclosure, each of surfaces 706, 708 is orthogonal to rays 712 and thereby tangent to the hypothetical sphere 710 at this location. Hypothetical sphere 710 is at a first radius that corresponds with rays 712, passing from center 142 to surfaces 706, 708, 718, and 720. Likewise, the other neighboring support structures 722 also include their two centermost sets of surfaces that are also at a distance corresponding to rays 712. As such, at a distance defined by ray 712, arcs 724 define a spherical surface of hypothetical sphere 710 that passes to and is tangent to each of surfaces 706, 708, 718, and 720, as well as those corresponding surfaces on support structures 722. And, it is evident that, due to the curved nature of hypothetical sphere 710, it is also clear that a slight angle 726 is formed between neighboring support structures 704, 716, as well as between the those and the additional structures 722. Other spherical arrangements also are generated between the other surfaces as well, such as surfaces 728 and 730, as well as the neighboring and corresponding surfaces that correspond with their respective arcs 724. Also, surfaces 740 and 742 create another spherical arrangement, as well as the neighboring and corresponding surfaces that correspond with their respective arcs 724. As such, to minimize the propensity for gaps to form at exemplary locations 707, as well as at further exemplary locations between neighboring support structures 722 and between other mini-modules along Z, stepped radii for each subsequent support structure are provided according to the disclosure.

That is, each of surfaces 706, 708, spanning a center point or center 709, are positioned at the same radius or distance along ray 712, from center 142. Surfaces 728, 730 are each positioned at a second radius or distance along rays 732 and at a distance that is greater than for that of surfaces 706, 708. Surfaces 740 and 742 are each positioned at a third radius or distance along rays 742 and at a distance that is greater than for that of surfaces 728, 730. All such surfaces are positioned along arcs 724 that correspond with each respective distance from center 142. The pattern continues and a fourth set of surfaces, outward in Z to either side of center 709 from surfaces 740, 742 are likewise positioned (surfaces 744) along arcs 724 and at a radial distance that is greater than that for surfaces 740, 742. And, although four distances (712, 732, 742, and 744) are shown, it is contemplated that more than four sets of surfaces at different radial distances may be included as well. Thus, support structure 704 includes another plurality of mini-module support surfaces 728, 730, each of mini-module support surfaces 728, 730 being tangent to center 142 of hypothetical sphere 710 and at a second distance 732 from center 142 of hypothetical sphere 710. Also, second support structure 716 includes a plurality of mini-module support surfaces 734, 736, each of mini-module support surfaces 734, 736, being tangent to center of the hypothetical sphere and at the second distance from the center of the hypothetical sphere.

Support structure 704 includes another plurality of mini-module support surfaces 728, 730, each of mini-module support surfaces 728, 730 being tangent to hypothetical sphere 710 and at a distance 732 from center 142 of hypothetical sphere 710. Support structure 716 includes mini-module support surfaces 734, 736, each of mini-module support surfaces 734, 736, being tangent to hypothetical sphere 710 and at distance 732 from center 142 of hypothetical sphere 710. Support structure 704 includes a first profile, as viewed in direction 738 and in the Y-Z plane and as seen in FIG. 5, and second support structure 716 includes the same profile as the first profile. In other words, and referring to FIG. 5, the profile is seen in direction 738 and of support structure 500 therein, which corresponds to support structure 704 of FIG. 7. The first profile thereby includes at least surfaces 502, 504, 506, 508, 510, 512, 514, 516, 518, side surfaces 520, and bottom surface 522. As such, though support structures 704, 716 may or may not include all the same features, according to one example they both include the same profile as defined by the relationship between surfaces 502, 504, 506, 508, 510, 512, 514, 516, 518, side surfaces 520, and bottom surface 522.

Thus, support structure 704 includes two centermost surfaces 706, 708 of its plurality of mini-module support surfaces and at distance 712 from center 152 of hypothetical sphere 710. Support structure 704 includes first adjacent surface 728 of the plurality of surfaces that is adjacent to and offset in a Z-direction from one of the two centermost surfaces 706, 708, and a second adjacent surface 730 of the plurality of surfaces that is adjacent to and offset in the Z-direction from the other of the two centermost surfaces 706, 708.

First support structure 704 includes another adjacent surface 740 that is adjacent to and offset in the Z-direction from the first adjacent surface 728, the another adjacent surface 740 at a third distance 742 from center 714 of hypothetical sphere 710, the third adjacent surface 718 being tangent to hypothetical sphere 710, as well as in the related detectors following the corresponding arc 724. First support structure 704 includes yet another adjacent surface 742 that is adjacent to and offset in the Z-direction from second adjacent surface 730, the adjacent surface 742 also at third distance 742 from center 714 of hypothetical sphere 710, adjacent surface 742 being tangent to hypothetical sphere 710 and following their corresponding arcs 724. Yet an additional set of surfaces are formed that are equidistant from center 714, to the surfaces yet further in Z from surfaces 740, 742, forming yet additional spherical detector surfaces along their respective arcs 724 and in the neighboring support structures 722. In fact, any number of steps may be so formed, and is not limited to the surfaces at the illustrated four surfaces (e.g., 708/706, 728/730, 740/742, etc. . . . ) and along their respective arcs 724, but any number of greater than or less than four distances is contemplated, according to the disclosure.

According to the disclosure and as seen in FIG. 7, second distance 732 is greater than first distance 712. Also, according to the disclosure and as seen in FIG. 7, third distance 742 is greater than second distance 732. FIG. 8 illustrates a plurality of detector sub-assemblies 800 side-by-side and each having a plurality of mini-modules positioned thereon. The detectors being positioned spherically at the four radial or spherical locations are visible and evident in detector sub-assemblies 800.

FIG. 9 illustrates a perspective view 900 of a CT detector that includes a plurality of mini-modules, each positioned according to the disclosure and on the mini-module support surfaces, a second plurality of mini-module surfaces, a third plurality of mini-module surfaces, and a fourth plurality of mini-module surfaces, forming the detector assembly as a multi-spherical detector in the CT system. Thus, as seen therein, because of the radially stepped nature of each subsequent mini-module, along the Z-axis, and stepping up in radius for each subsequent mini-module, any gap between mini-modules in the X-direction is thereby minimized according to the disclosure.

According to the disclosure, a method of assembling a detector assembly for a CT system includes providing a first support structure having a first plurality of mini-module support surfaces, each of the first plurality of mini-module support surfaces being tangent to a hypothetical sphere that is formed having a center of the hypothetical sphere positioned at a focal spot of the CT system, the first plurality of mini-module support surfaces at a first distance from the center of the hypothetical sphere, providing a second support structure having a second plurality of mini-module surfaces, and positioning the second support structure to be angled in an X-Y plane with respect to the first support structure and such that the second plurality of mini-module surfaces are tangent to the hypothetical sphere and at the first distance from the center of the hypothetical sphere.

According to the disclosure, CT system 100 includes a rotatable gantry 102 having an opening 104 for receiving an object to be scanned, an x-ray tube 114 having a focal spot 142 from which x-rays emit, and a detector assembly 130 one or more mini-modules for receiving x-rays from the focal spot, the detector assembly 900 includes aspects and disclosure corresponding to the figures and description above and including the description and disclosure as related to FIGS. 5, 6, 7, and 8, and detector assembly 900 corresponds with detector assembly 130 as shown in FIG. 1 and subsequently described also in FIGS. 2, 3, and 4.

As such, according to the disclosure, a detector assembly for a CT system includes a first support structure having a first plurality of mini-module support surfaces, each of the first plurality of mini-module support surfaces being tangent to a hypothetical sphere that is formed having a center of the hypothetical sphere positioned at a focal spot of the CT system, the first plurality of mini-module support surfaces at a first distance from the center of the hypothetical sphere, and a second support structure positioned next to the first support structure and having a second plurality of mini-module surfaces, the second support structure being angled in an X-Y plane with respect to the first support structure such that the second plurality of mini-module surfaces are tangent to the hypothetical sphere and at the first distance from the center of the hypothetical sphere.

Also according to the disclosure, a method of assembling a detector assembly for a CT system includes providing a first support structure having a first plurality of mini-module support surfaces, each of the first plurality of mini-module support surfaces being tangent to a hypothetical sphere that is formed having a center of the hypothetical sphere positioned at a focal spot of the CT system, the first plurality of mini-module support surfaces at a first distance from the center of the hypothetical sphere, providing a second support structure having a second plurality of mini-module surfaces, and positioning the second support structure to be angled in an X-Y plane with respect to the first support structure and such that the second plurality of mini-module surfaces are tangent to the hypothetical sphere and at the first distance from the center of the hypothetical sphere.

Still further, according to the disclosure, a CT system includes a rotatable gantry having an opening for receiving an object to be scanned, an x-ray tube having a focal spot from which x-rays emit, and a detector assembly comprising one or more scintillator modules for receiving x-rays from the focal spot. The detector assembly includes a first support structure having a first plurality of mini-module support surfaces, each of the first plurality of mini-module support surfaces being tangent to a hypothetical sphere that is formed having a center of the hypothetical sphere positioned at a focal spot of the CT system, the first plurality of mini-module support surfaces at a first distance from the center of the hypothetical sphere, and a second support structure positioned next to the first support structure and having a second plurality of mini-module surfaces, the second support structure being angled in an X-Y plane with respect to the first support structure such that the second plurality of mini-module surfaces are tangent to the hypothetical sphere and at the first distance from the center of the hypothetical sphere.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Further-more, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection or imaging techniques.

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A detector assembly for a CT system, comprising:
    a first support structure having a first plurality of mini-module support surfaces, each of the first plurality of mini-module support surfaces being tangent to a hypothetical sphere that is formed having a center of the hypothetical sphere positioned at a focal spot of the CT system, the first plurality of mini-module support surfaces at a first distance from the center of the hypothetical sphere; and
    a second support structure positioned next to the first support structure and having a second plurality of mini-module surfaces, the second support structure being angled in an X-Y plane with respect to the first support structure such that the second plurality of mini-module surfaces are tangent to the hypothetical sphere and at the first distance from the center of the hypothetical sphere.

2. The detector assembly of claim 1, further comprising:
    the first support structure having a third plurality of mini-module support surfaces, each of the third plurality of mini-module support surfaces being tangent to the hypothetical sphere and at a second distance from the center of the hypothetical sphere; and
    the second support structure having a fourth plurality of mini-module support surfaces, each of the fourth plurality of mini-module support surfaces being tangent to the hypothetical sphere and at the second distance from the center of the hypothetical sphere.

3. The detector assembly of claim 2, wherein the first support structure includes a first profile in A Y-Z plane, and the second support structure includes the same profile as the first profile.

4. The detector assembly of claim 2, wherein the first support structure includes:
    two centermost surfaces of the first plurality of mini-module support surfaces at the first distance from the center of the hypothetical sphere;
    a first adjacent surface of the third plurality of surfaces that is adjacent to and offset radially and also in a Z-direction from one of the two centermost surfaces; and
    a second adjacent surface of the third plurality of surfaces that is adjacent to and offset radially and also in the Z-direction from the other of the two centermost surfaces.

5. The detector assembly of claim 4, wherein the first support structure includes:
    a third adjacent surface that is adjacent to and offset radially and also in the Z-direction from the first adjacent surface, the third adjacent surface at a third distance from the center of the hypothetical sphere, the third adjacent surface being tangent to the hypothetical sphere; and
    a fourth adjacent surface that is adjacent to and offset radially and also in the Z-direction from the second adjacent surface, the fourth adjacent surface at the third distance from the center of the hypothetical sphere, the fourth adjacent surface being tangent to the hypothetical sphere.

6. The detector assembly of claim 5, wherein the second distance is greater than the first distance.

7. The detector assembly of claim 6, wherein the third distance is greater than the second distance.

8. A method of assembling a detector assembly for a CT system, the method comprising:
    providing a first support structure having a first plurality of mini-module support surfaces, each of the first plurality of mini-module support surfaces being tangent to a hypothetical sphere that is formed having a center of the hypothetical sphere positioned at a focal spot of the CT system, the first plurality of mini-module support surfaces at a first distance from the center of the hypothetical sphere;
    providing a second support structure having a second plurality of mini-module surfaces; and
    positioning the second support structure to be angled in an X-Y plane with respect to the first support structure and such that the second plurality of mini-module surfaces are tangent to the hypothetical sphere and at the first distance from the center of the hypothetical sphere.

9. The method of claim 8, further comprising:
    providing the first support structure having a third plurality of mini-module support surfaces, each of the third plurality of mini-module support surfaces being tangent to the hypothetical sphere and at a second distance from the center of the hypothetical sphere; and
    positioning the second support structure includes positioning having a fourth plurality of mini-module support surfaces, each of the fourth plurality of mini-module support surfaces being tangent to the hypothetical sphere and at the second distance from the center of the hypothetical sphere.

10. The method of claim 9, wherein the first support structure includes a first profile in a Y-Z plane, and the second support structure includes the same profile as the first profile.

11. The method of claim 9, wherein providing the first support structure includes:
    providing two centermost surfaces of the first plurality of mini-module support surfaces at the first distance from the center of the hypothetical sphere;

providing a first adjacent surface of the third plurality of surfaces that is adjacent to and offset radially and also in a Z-direction from one of the two centermost surfaces; and providing a second adjacent surface of the third plurality of surfaces that is adjacent to and offset radially and also in the Z-direction from the other of the two centermost surfaces.

12. The method of claim 11, wherein providing the first support structure includes:

providing a third adjacent surface that is adjacent to and offset radially and also in the Z-direction from the first adjacent surface, the third adjacent surface at a third distance from the center of the hypothetical sphere, the third adjacent surface being tangent to the hypothetical sphere;

providing a fourth adjacent surface that is adjacent to and offset radially and also in the Z-direction from the second adjacent surface, the fourth adjacent surface at the third distance from the center of the hypothetical sphere, the fourth adjacent surface being tangent to the hypothetical sphere.

13. The method of claim 12, wherein the second distance is greater than the first distance, and the third distance is greater than the second distance.

14. A CT system comprising:

a rotatable gantry having an opening for receiving an object to be scanned;

an x-ray tube having a focal spot from which x-rays emit; and a detector assembly comprising one or more mini-modules modules for receiving x-rays from the focal spot, the detector assembly comprising:

a first support structure having a first plurality of mini-module support surfaces, each of the first plurality of mini-module support surfaces being tangent to a hypothetical sphere that is formed having a center of the hypothetical sphere positioned at a focal spot of the CT system, the first plurality of mini-module support surfaces at a first distance from the center of the hypothetical sphere; and a second support structure positioned next to the first support structure and having a second plurality of mini-module surfaces, the second support structure being angled in an X-Y plane with respect to the first support structure such that the second plurality of mini-module surfaces are tangent to the hypothetical sphere and at the first distance from the center of the hypothetical sphere.

15. The CT system of claim 1, the detector assembly further comprising:

the first support structure having a third plurality of mini-module support surfaces, each of the third plurality of mini-module support surfaces being tangent to the hypothetical sphere and at a second distance from the center of the hypothetical sphere; and the second support structure having a fourth plurality of mini-module support surfaces, each of the fourth plurality of mini-module support surfaces being tangent to the hypothetical sphere and at the second distance from the center of the hypothetical sphere.

16. The CT system of claim 15, wherein the first support structure includes a first profile in a Y-Z plane, and the second support structure includes the same profile as the first profile.

17. The CT system of claim 15, wherein the first support structure includes:

two centermost surfaces of the first plurality of mini-module support surfaces at the first distance from the center of the hypothetical sphere;

a first adjacent surface of the third plurality of surfaces that is adjacent to and offset radially and also in a Z-direction from one of the two centermost surfaces; and a second adjacent surface of the third plurality of surfaces that is adjacent to and offset radially and also in the Z-direction from the other of the two centermost surfaces.

18. The CT system of claim 17, wherein the first support structure includes:

a third adjacent surface that is adjacent to and offset radially and also in the Z-direction from the first adjacent surface, the third adjacent surface at a third distance from the center of the hypothetical sphere, the third adjacent surface being tangent to the hypothetical sphere; and a fourth adjacent surface that is adjacent to and offset radially and also in the Z-direction from the second adjacent surface, the fourth adjacent surface at the third distance from the center of the hypothetical sphere, the fourth adjacent surface being tangent to the hypothetical sphere.

19. The CT system of claim 18, wherein the second distance is greater than the first distance, and the third distance is greater than the second distance.

20. The CT system of claim 19, further comprising a plurality of mini-modules, each positioned on the first plurality of mini-module support surfaces, the second plurality of mini-module surfaces, the third plurality of mini-module surfaces, and the fourth plurality of mini-module surfaces, forming the detector assembly as a multi-spherical detector in the CT system.

* * * * *